United States Patent
Williams

(10) Patent No.: US 9,364,236 B2
(45) Date of Patent: Jun. 14, 2016

(54) SLANTED INTRODUCER FOR END-TO-END ANASTOMOSIS ANVIL

(71) Applicant: Covidien LP, Mansfield, MA (US)

(72) Inventor: Justin Williams, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 679 days.

(21) Appl. No.: 13/673,170

(22) Filed: Nov. 9, 2012

(65) Prior Publication Data

US 2014/0131415 A1 May 15, 2014

(51) Int. Cl.
- *A61B 17/115* (2006.01)
- *A61B 17/11* (2006.01)
- *A61B 17/00* (2006.01)

(52) U.S. Cl.
CPC ............. *A61B 17/11* (2013.01); *A61B 17/1155* (2013.01); *A61B 46/13* (2016.02); *A61B 46/17* (2016.02); *A61B 2017/00336* (2013.01); *A61B 2017/111* (2013.01); *A61B 2017/1132* (2013.01)

(58) Field of Classification Search
CPC .... A61B 17/00; A61B 17/068; A61B 17/115; A61B 17/11; A61B 17/04; A61B 17/10; A61B 17/064; A61B 2017/00473; A61B 2017/00336; A61B 2017/00623; A61B 2017/1205; A61B 2017/22045; A61B 2017/00154
USPC .............. 227/19, 175.1–182.1; 606/170, 148, 606/139
See application file for complete search history.

(56) References Cited

U.S. PATENT DOCUMENTS

| | | | |
|---|---|---|---|
| 5,626,597 A | 5/1997 | Urban et al. | |
| 5,857,999 A | 1/1999 | Quick et al. | |
| 6,764,464 B2 | 7/2004 | McGuckin, Jr. et al. | |
| 7,431,191 B2 | 10/2008 | Milliman | |
| 7,516,877 B2 | 4/2009 | Aranyi | |
| 7,582,071 B2 | 9/2009 | Wenchell | |
| 7,846,149 B2 | 12/2010 | Jankowski | |
| 7,896,847 B2 | 3/2011 | Wenchell | |
| 8,136,711 B2 | 3/2012 | Beardsley et al. | |
| 8,235,947 B2 | 8/2012 | Wenchell | |
| 2004/0066008 A1 | 4/2004 | Smith | |
| 2005/0143756 A1 | 6/2005 | Jankowski | |
| 2005/0187576 A1* | 8/2005 | Whitman et al. | ............. 606/219 |
| 2007/0051375 A1 | 3/2007 | Milliman | |
| 2009/0204108 A1* | 8/2009 | Steffen | ............................. 606/1 |
| 2010/0030256 A1* | 2/2010 | Dubrul | ............... A61B 10/0266 606/200 |

(Continued)

FOREIGN PATENT DOCUMENTS

WO    WO 03/030745 A1    4/2003

OTHER PUBLICATIONS

Extended European Search Report dated Feb. 28, 2014 for EP 13 19 2100.

(Continued)

*Primary Examiner* — Hemant M Desai
*Assistant Examiner* — Mary Hibbert

(57) ABSTRACT

A surgical stapling device including an elongated body portion having a proximal end and a distal end, and defining a longitudinal axis therethrough is presented. The surgical stapling device further includes a handle assembly positionable adjacent the body portion at the proximal end thereof and an introducer assembly positioned at the distal end of the body portion. The introducer assembly includes a sleeve positionable over at least a portion of a shell, the sleeve having a slanted distal end configured to receive a slanted membrane thereon.

24 Claims, 13 Drawing Sheets

(56) References Cited

U.S. PATENT DOCUMENTS

| | | |
|---|---|---|
| 2010/0038401 A1 | 2/2010 | Milliman et al. |
| 2011/0114700 A1 | 5/2011 | Baxter, III et al. |
| 2012/0138661 A1 | 6/2012 | Beardsley et al. |

OTHER PUBLICATIONS

European Office Action for European Appln. No. EP 13192100.9 dated Sep. 15, 2015.

* cited by examiner

SLANTED INTRODUCER FOR END-TO-END ANASTOMOSIS ANVIL

BACKGROUND

1. Technical Field

The present disclosure relates to a surgical instrument for applying surgical fasteners or staples to body tissue, and more particularly, to an introducer assembly for use with an end-to-end anastomosis stapling apparatus.

2. Background of Related Art

Anastomosis is a surgical joining of separate hollow organ sections. Typically, an anastomosis procedure follows surgery in which a diseased or defective section of hollow tissue is removed and the remaining end sections are joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Typically, these instruments include an elongated shaft having a handle portion at a proximal end to actuate the instrument and a staple holding component disposed at a distal end. An anvil assembly including an anvil shaft with attached anvil head is mounted to the distal end adjacent the staple holding component. Opposed end sections of the organ to be stapled are clamped between the anvil head and the staple holding component. The clamped tissue is stapled by driving a plurality of staples from the staple holding component so that the ends of the staples pass through the tissue and are deformed by the anvil head.

In use, one end section of the organ is secured about the anvil assembly and the other end section of the organ is held in place adjacent the staple holding component. The shaft of the anvil assembly is removably connected to the instrument. Once the anvil shaft is secured to the instrument, the anvil is drawn into close approximation to the staple holding component. The instrument is then fired to cause the staples to pass through tissue of both sections of the organ and deform against the anvil. During the firing step, a circular knife is advanced to cut tissue inside the staple line, thereby establishing a passage between the two sections of the organ. After firing, the instrument is typically removed by withdrawing the anvil through the staple line, after which the surgeon carefully inspects the surgical site to ensure a proper anastomosis has been achieved.

While circular staplers are helpful in a number of surgical procedures, problems such as anastomotic leak, tear of tissue during stapler extraction, bleeding, and other complications may arise. Another issue relates to the contamination of the circular stapler.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

In accordance with an embodiment of the present disclosure, there is provided a surgical stapling device. The surgical stapling device includes an elongated body portion having a proximal end and a distal end, and defining a longitudinal axis therethrough, a handle assembly positionable adjacent the body portion at the proximal end thereof and an introducer assembly positioned at the distal end of the body portion. The introducer assembly includes a sleeve positionable over at least a portion of a shell, the sleeve having a slanted distal end configured to receive a slanted membrane thereto.

In an embodiment, a releaser component is positioned between the sleeve and the shell, the releaser component including a plurality of outwardly protruding tabs circumferentially disposed thereon and a plurality of cables circumferentially attached thereto.

In another embodiment, a portion of the releaser component having the plurality of cables circumferentially attached thereto extends beyond a proximal end of the sleeve. When a force is applied to the plurality of cables, the releaser component is slidingly displaced along the longitudinal axis of the body portion to remove the sleeve from the shell. In other words, the plurality of outwardly protruding tabs of the releaser component are lifted to disengage the slanted sleeve from the shell during retraction of the slanted sleeve.

In yet another embodiment, the sleeve includes a plurality of first slots and a plurality of second slots circumferentially disposed at a proximal end thereof.

The plurality of second slots are configured to cooperate with a plurality of respective sleeve tabs extending therethrough, the plurality of sleeve tabs configured to secure the sleeve to the shell.

In another embodiment, the plurality of sleeve tabs are forward facing tabs disposed at one end of the sleeve and rearward facing tabs disposed at the other end of the sleeve such that the sleeve moves longitudinally or axially within a predetermined region defined by a distance between the forward facing and backward facing tabs.

The plurality of first slots are configured to cooperate with the plurality of outwardly protruding tabs of the releaser component.

In yet another embodiment, the shell includes at least one groove extending circumferentially therearound for allowing the shell to rotate. Alternatively, the shell includes a plurality of grooves circumferentially disposed in equally spaced apart intervals thereon for inhibiting the shell from rotating.

In another embodiment, the slanted membrane includes a slit extending a length of the slanted membrane.

In accordance with another embodiment of the present disclosure, there is provided an introducer assembly. The introducer assembly includes a shell, a sleeve configured to be inserted over at least a portion of the shell and a release mechanism configured to be positioned between the shell and the sleeve.

In an embodiment, the sleeve is a slanted sleeve configured to receive a slanted membrane having a slit thereto.

In another embodiment, the release mechanism includes a plurality of outwardly protruding tabs circumferentially disposed thereon and a plurality of cables circumferentially attached thereto.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

Various embodiments of the present disclosure are described hereinbelow with reference to the drawings, wherein.

Figure 1:
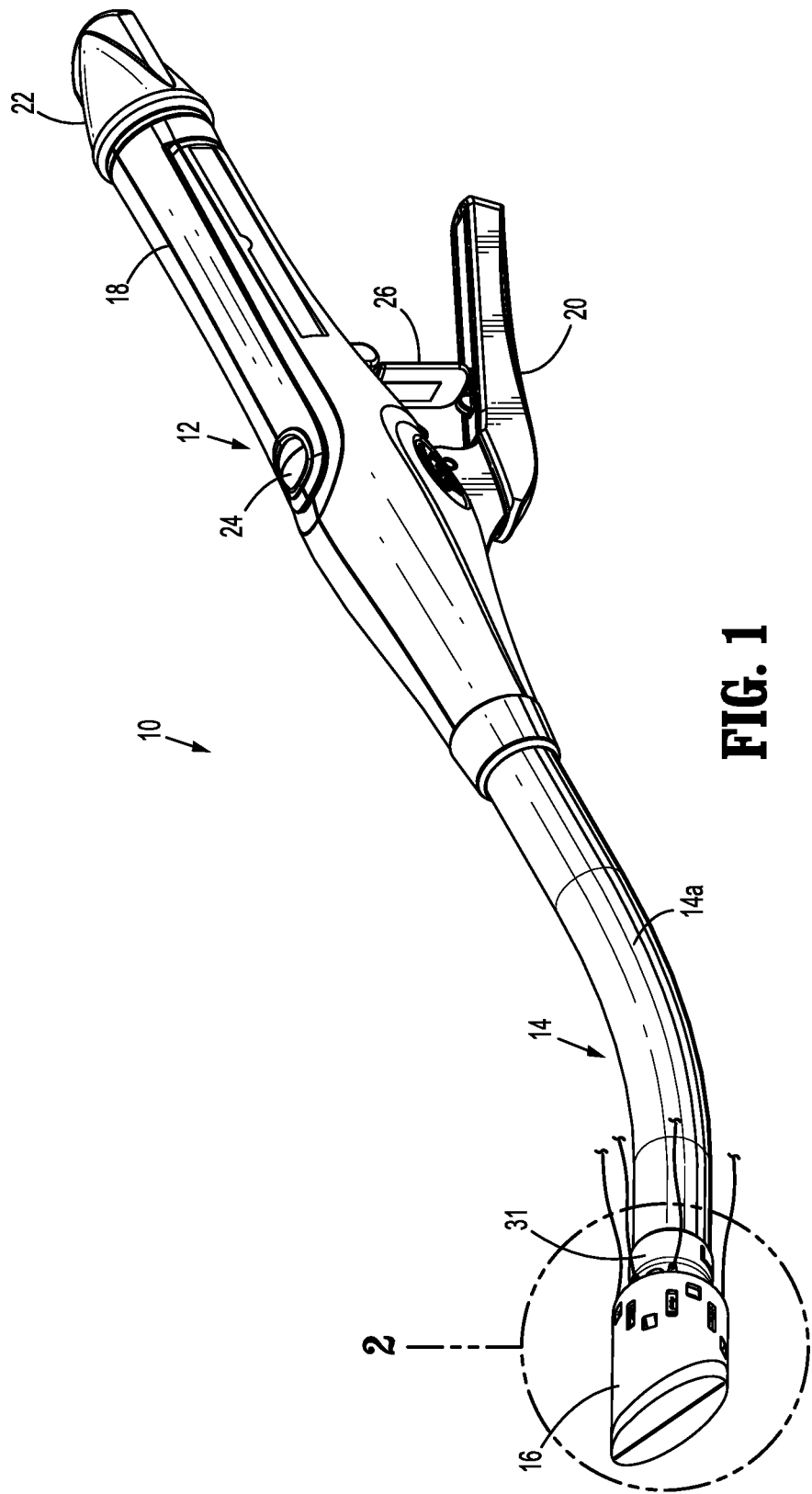
FIG. 1 is a perspective view of a surgical stapling device including an introducer sleeve distally disposed thereof, in accordance with an embodiment of the present disclosure.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION OF EMBODIMENTS

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

Reference to embodiments of the present disclosure will now be made in detail. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments will be described below while referencing the accompanying figures. The accompanying figures are merely examples and are not intended to limit the scope of the present disclosure.

Figure 23:
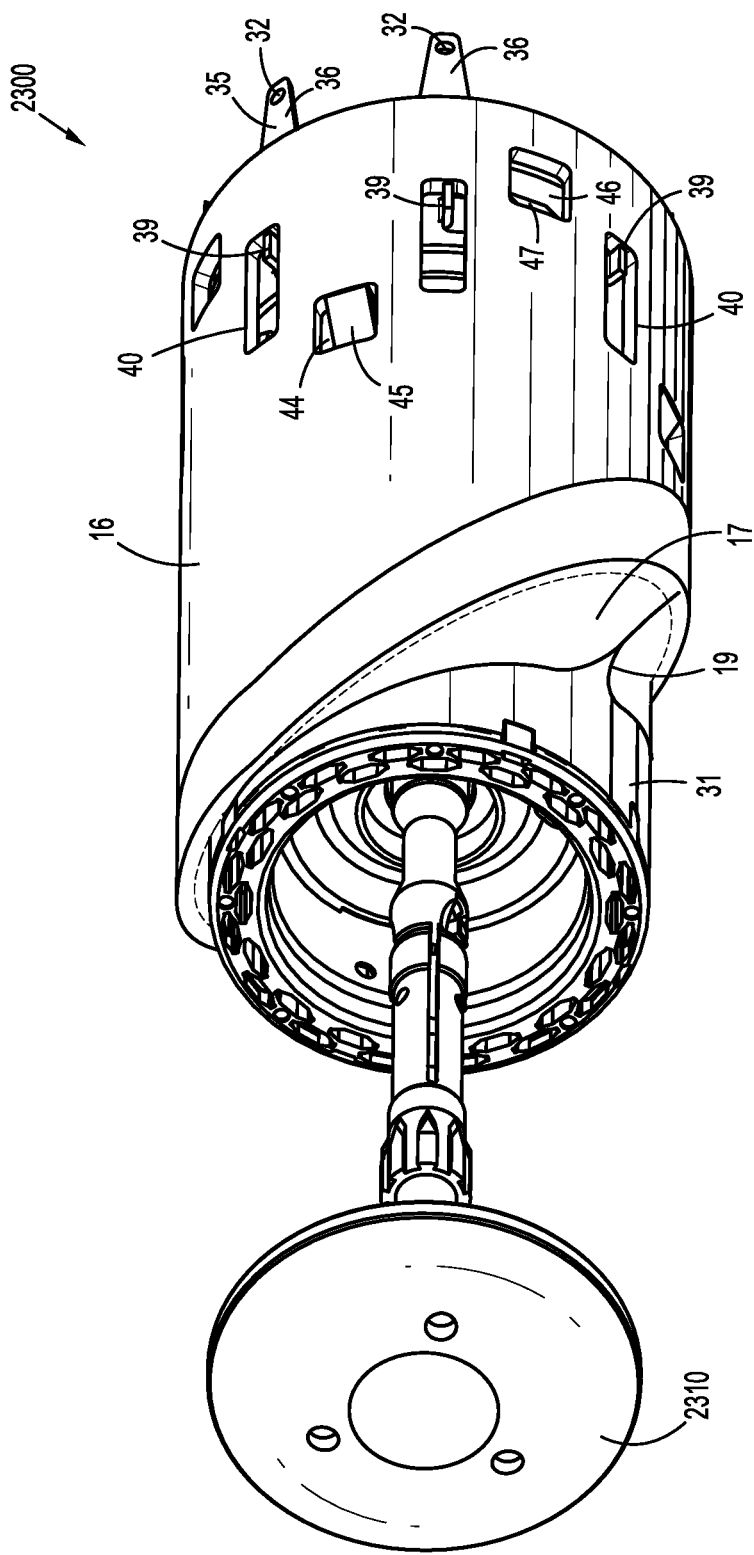
FIG. 23 illustrates an anvil assembly inserted through the introducer assembly, in accordance with an embodiment of the present disclosure.

FIG. 1 illustrates an embodiment of a surgical stapling device 10 configured for use with a tilt anvil assembly 2300 (see FIG. 23). Briefly, surgical stapling device 10 includes a proximal handle assembly 12, an elongated central body portion 14 including a curved elongated outer tube 14a, and a sleeve 16. Alternately, in some surgical procedures, e.g., the treatment of hemorrhoids, it is desirable to have a substantially straight, shortened, central body portion. The length, shape and/or the diameter of body portion 14 and sleeve 16 may also be varied to suit a particular surgical procedure.

With further reference to FIG. 1, handle assembly 12 includes a stationary handle 18, a firing trigger 20, a rotatable approximation knob 22 and an indicator 24. A pivotally mounted trigger lock 26 is fastened to handle assembly 12 and is manually positioned to inhibit inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Sleeve 16 cooperates with a shell assembly 31, which will be described in detail below.

Handle assembly 12 may be actuated to approximate anvil assembly 2300 (see FIG. 23) relative to a staple cartridge assembly (not shown) and to apply a pair of annular arrays of staples (not shown) through tissue. In order to properly position tissue in anvil assembly 2300, rotatable knob 22 may be rotated to move anvil assembly 2300 axially relative to staple cartridge assembly between a spaced apart position and an approximated position in which anvil assembly 2300 is positioned adjacent staple cartridge assembly to clamp tissue therebetween. Handle members 18, 20 may be squeezed to fire staples through tissue. Moreover, elongated body portion 14 is constructed to have a slightly curved/bent shape along its length. However, elongated body portion 14 may also be straight, as well as flexible to bend to any configuration. The length, shape and/or the diameter of elongated body portion 14 may be varied to suit a particular surgical procedure.

Figure 2:
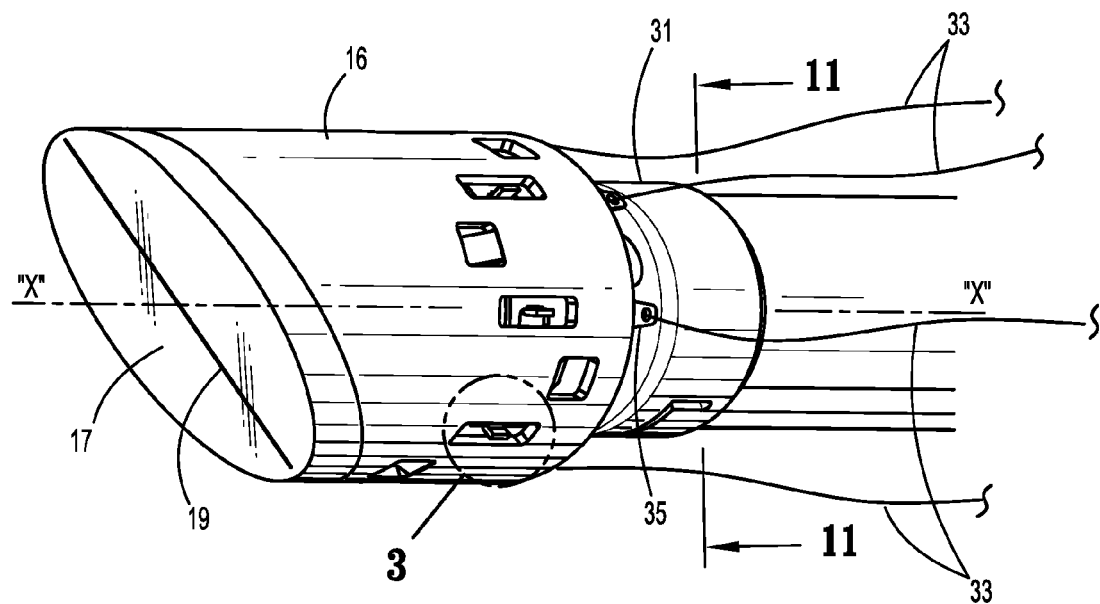
FIG. 2 is an area of detail of FIG. 1 depicting a perspective view of the introducer sleeve, in accordance with an embodiment of the present disclosure.

Referring to FIG. 2, a perspective view of the introducer sleeve 16, in accordance with an embodiment of the present disclosure is presented.

Figure 3:
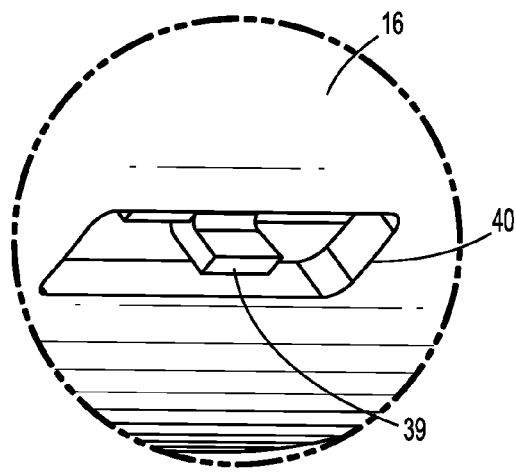
FIG. 3 is an area of detail of FIG. 2 depicting a releaser tab protruding from a slot in the introducer sleeve, in accordance with an embodiment of the present disclosure.

The introducer sleeve 16 includes a membrane 17 disposed on a distal end thereof. The membrane 17 includes a slit 19 extending the diameter of the membrane 17. The proximal end of the sleeve 16 is at least partially positioned over a shell 31. A releaser component 35 is placed between the sleeve 16 and the shell 31. The releaser component 35 includes a plurality of cables 33 connected at a distal end thereof. Referring to FIG. 3, an enlarged view of a releaser tab 39 protruding from a slot 40 in the introducer sleeve 16, in accordance with an embodiment of the present disclosure is presented.

In one exemplary embodiment, the introducer sleeve 16 is slanted. As such, the membrane 17 is also slanted in order to engage the distal end of the sleeve 16. Stated differently, the distal end of the sleeve 16 and the membrane 17 may be oblique, tilted, angled or non-level with respect to axis "X."

Figure 4:
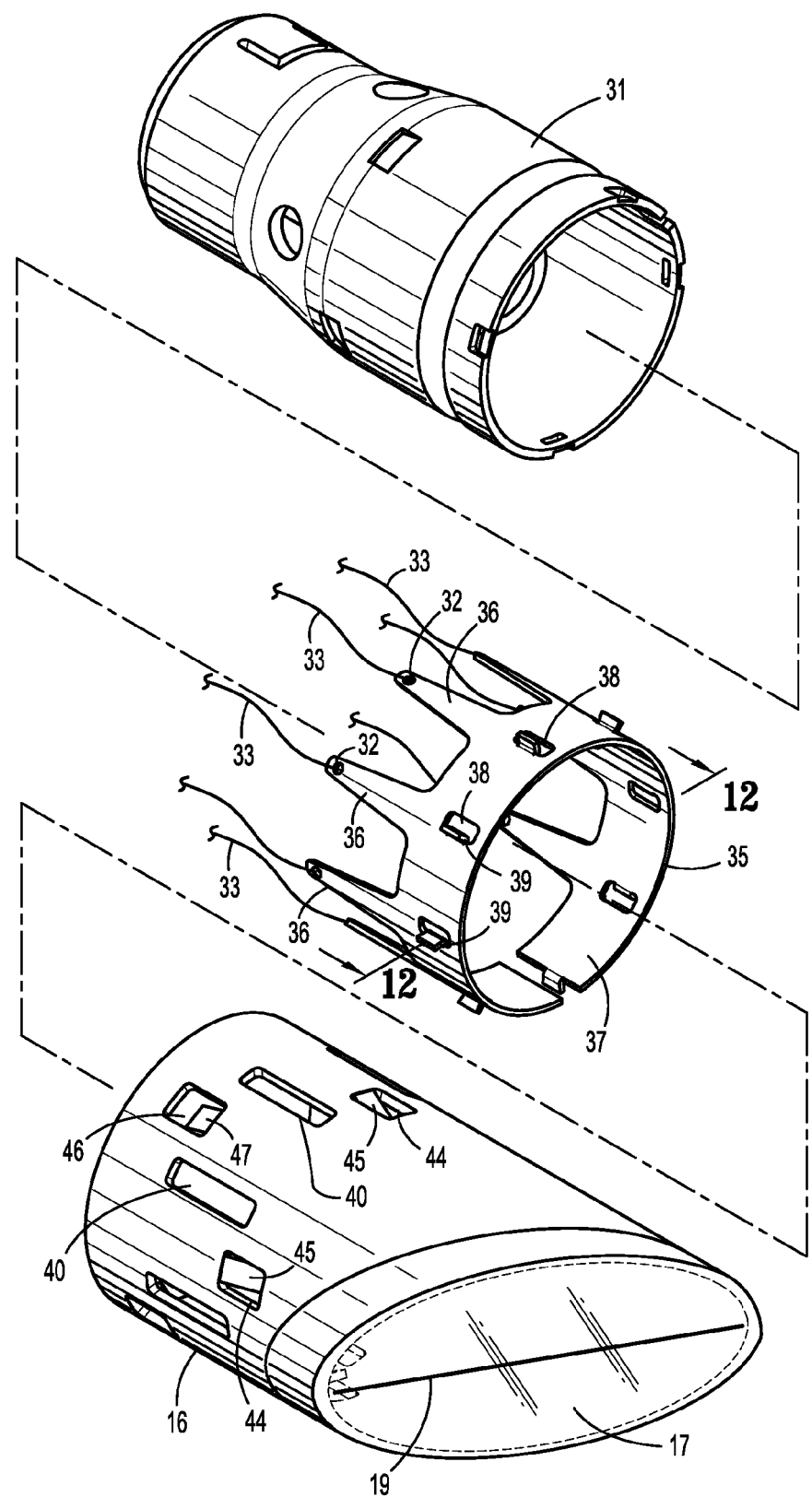
FIG. 4 is an exploded perspective view of the shell, release component, and introducer sleeve, in accordance with an embodiment of the present disclosure.

Referring to FIG. 4, an exploded perspective view of the shell 31, release component 35, and introducer sleeve 16, in accordance with an embodiment of the present disclosure is presented.

As noted above with reference to FIG. 2, the sleeve 16 is positioned over the releaser component 35, which in turn is positioned over the shell 31. In particular, a portion of the sleeve 16 is placed over the releaser component 35, and a portion of the releaser component 35 is placed over the shell 31.

The releaser component 35 includes a body member 37 having a plurality of protrusions 36 extending therefrom. The plurality of protrusions 36 may be triangular in nature to form a series of teeth. A distal end of each of the plurality of protrusions 36 includes an opening 32 for accommodating one end of a cable 33. The body member 37 may be a circular member that includes circumferentially and equally spaced apart openings 38. A releaser tab 39 may engage at least one side of each of the spaced apart openings 38.

The sleeve 16 includes a plurality of distal openings 44 and a plurality of proximal openings 46. Each of the plurality of distal openings 44 includes a tab 45 protruding from at least one side therefrom. Each of the plurality of proximal openings 46 includes a tab 47 protruding from at least one side therefrom. The plurality of distal openings 44 circumferentially envelop a distal area or region of the sleeve 16, whereas the plurality of proximal openings 46 circumferentially envelop a proximal area or region of the sleeve 16. The plurality of distal openings 44 and the plurality of proximal openings 46 are shown to have a square shape. Of course, one skilled in the art may contemplate a plurality of different shapes and sizes for such openings 44, 46. A plurality of slots 40 is circumferentially positioned around a mid-portion of the sleeve 16, such that the slots 40 are disposed between the plurality of distal openings 44 and the plurality of proximal openings 46. The plurality of slots 40 are shown to have a rectangular shape. Of course, one skilled in the art may contemplate a plurality of different shapes and sizes for such slots 40. Additionally, it is noted that the plurality of distal openings 44 are radially spaced with respect to the plurality of proximal openings 46. Also, the plurality of distal openings 44 and the plurality of proximal openings 46 are off-centered with respect to the plurality of slots 40.

Figure 5:
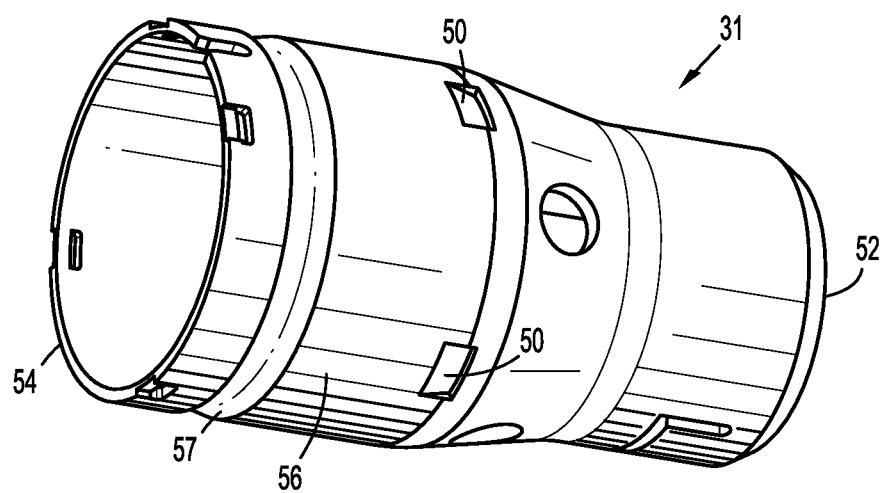
FIG. 5 is a perspective view of the shell of FIG. 4 illustrating a plurality of grooves circumferentially extending around the shell, in accordance with an embodiment of the present disclosure.

Referring to FIG. 5, a perspective view of the shell 31 of FIG. 4 illustrating a plurality of grooves 50 circumferentially extending around the shell 31, in accordance with an embodiment of the present disclosure is presented. The body 56 of the shell 31 includes a proximal end 52 and a distal end 54. The body 56 also includes a plurality of grooves 50 extending circumferentially around the body 56 at a midpoint of the body 56. The body 56 further includes a channel or ridge 57 extending circumferentially around the body 56 at the distal end 54. The plurality of grooves 50 inhibit the sleeve 16 from rotating once the sleeve 16 engages the shell 31. Additionally, the channel 57 inhibits the sleeve 16 from extending or moving beyond the distal end 54 of the shell 31. In other words, the channel 57 locks or secures the shell 31 to the sleeve 16.

Figure 6:
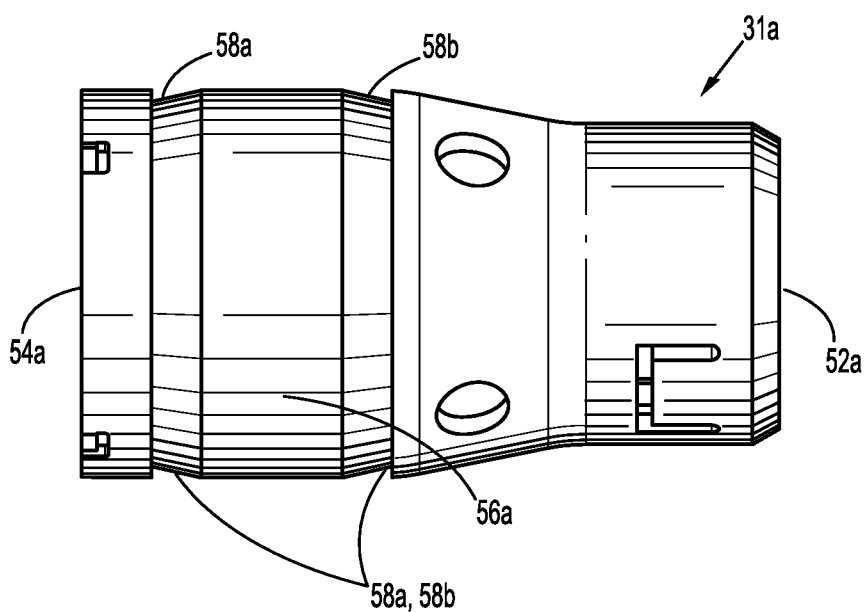
FIG. 6 is an alternate embodiment of FIG. 5, where the body portion of the shell includes two circumferential channels, in accordance with an embodiment of the present disclosure.

Referring to FIG. 6, an alternate embodiment of FIG. 5, where the body portion of the shell 31a includes two circumferential channels 58a, 58b, in accordance with an embodiment of the present disclosure is presented. In FIG. 6, the body 56a of the shell 31a includes a proximal end 52a and a distal end 54a. The body 56a also includes a first channel 58a extending circumferentially around the body 56a at a midpoint of the body 56 and a second channel 58b extending circumferentially around the body 56a at the distal end 54a. The second channel 58b inhibits the sleeve 16 from rotating once the sleeve 16 engages the shell 31. The first channel 58a inhibits the sleeve 16 from extending beyond the distal end 54a of the shell 31a. In other words, the first channel 58a locks or secures the shell 31a to the sleeve 16.

Figure 7:
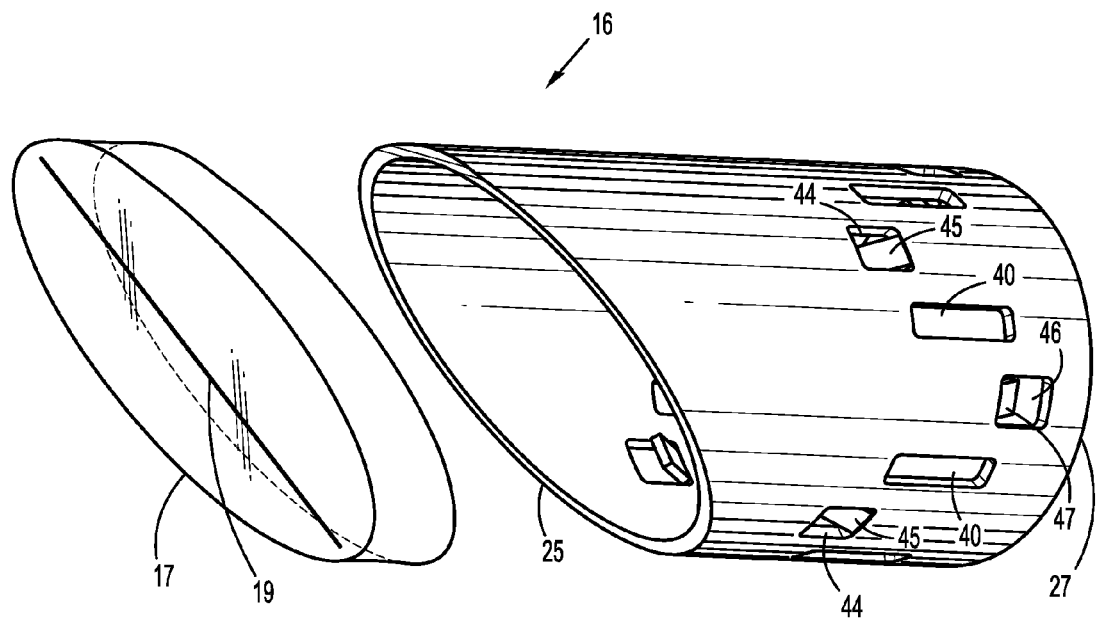
FIG. 7 is a perspective view of the introducer sleeve of FIG. 4, with the membrane shown detached from the introducer sleeve, in accordance with an embodiment of the present disclosure.
Figure 8:
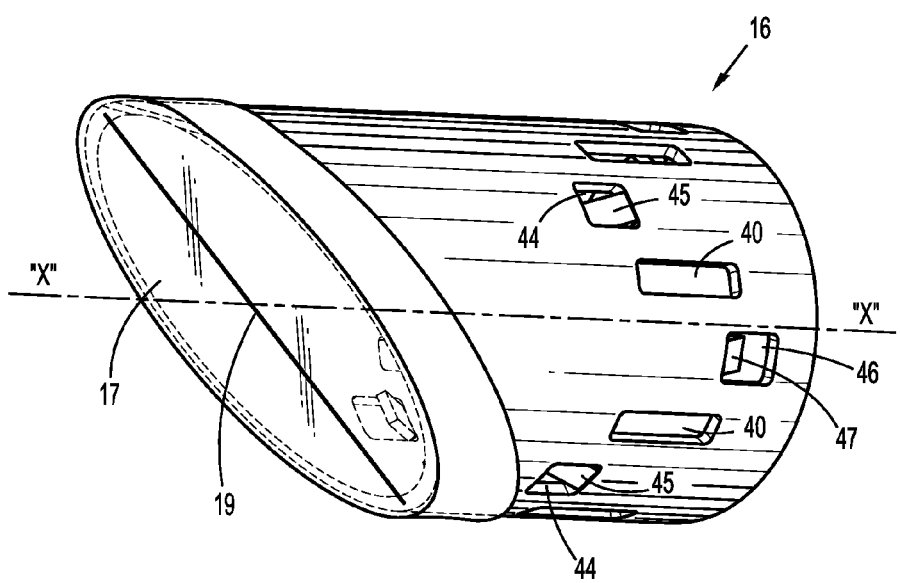
FIG. 8 is a perspective view of FIG. 7, with the membrane attached to the introducer sleeve, in accordance with an embodiment of the present disclosure.

Referring to FIG. 7, a perspective view of the introducer sleeve 16 of FIG. 4, with the membrane 17 shown detached from the introducer sleeve 16, in accordance with an embodiment of the present disclosure is presented. Referring to FIG. 8, a perspective view of FIG. 7, with the membrane 17 attached to the introducer sleeve 16, in accordance with an embodiment of the present disclosure is presented.

In the exploded view of FIG. 7, the sleeve 16 includes a distal end 25 and a proximal end 27. The distal end 25 is slanted or oblique or angled with respect to longitudinal axis "X" (see FIG. 8) extending through the sleeve 31. The distal end 25 is configured to receive or engage a membrane 17. The membrane 17 is also slanted or oblique or angled in order to fit over the distal end 25 of the sleeve 16. The angle of the membrane 17 with respect to a longitudinal axis "X" extending therethrough may be anywhere between 10° degrees and 120° degrees. In the exemplary embodiment of FIGS. 7 and 8, the angle is at 45° degrees with respect to the longitudinal axis "X." It is contemplated that the membrane need not be angled with respect to the longitudinal axis.

The proximal end 27 of the sleeve 16 is configured to engage shell 31, as discussed above with reference to FIGS. 5 and 6. In the assembled view of FIG. 8, the membrane 17 is connected to or mounted to or cooperates with the distal end 25 of the sleeve 16. The membrane 17 includes a slit 19. The slit 19 is shown in a straight configuration extending the length of the membrane 17. However, one skilled in the art may contemplate a plurality of different shapes and sizes for the slit 19. In addition, there may be more than one slit.

The membrane 17 is adapted and dimensioned to keep the end-to-end anastomosis (EEA) instrument clean from debris collected at the surgical site. The membrane 17 may be formed from a plurality of different elastic or elastomeric materials. The membrane 17 may be formed from any flexible and may include natural or synthetic fibers such as plastic, rubber, glass, or metal. Additionally, the membrane 17 may be a bio-absorbable or non-absorbable material, pad of material, composite materials, materials including fibers, collagen or other materials derived from natural tissue.

Figure 9:
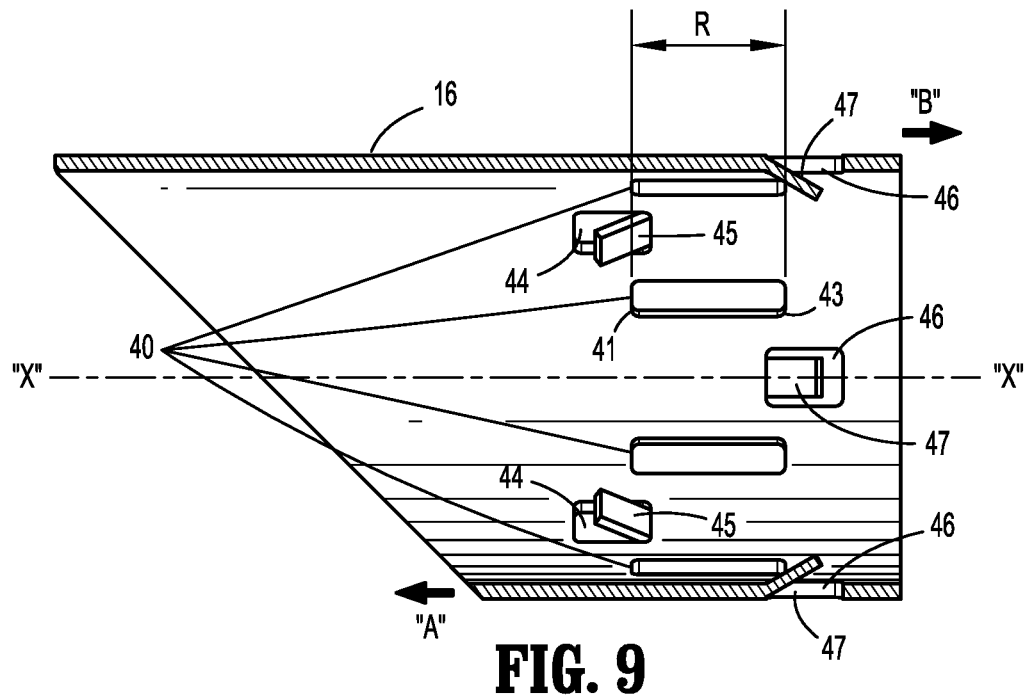
FIG. 9 is a cross-sectional view of the introducer sleeve illustrating the plurality of tabs of the shell extending from the plurality of slots of the introducer sleeve, in accordance with an embodiment of the present disclosure.
Figure 10:
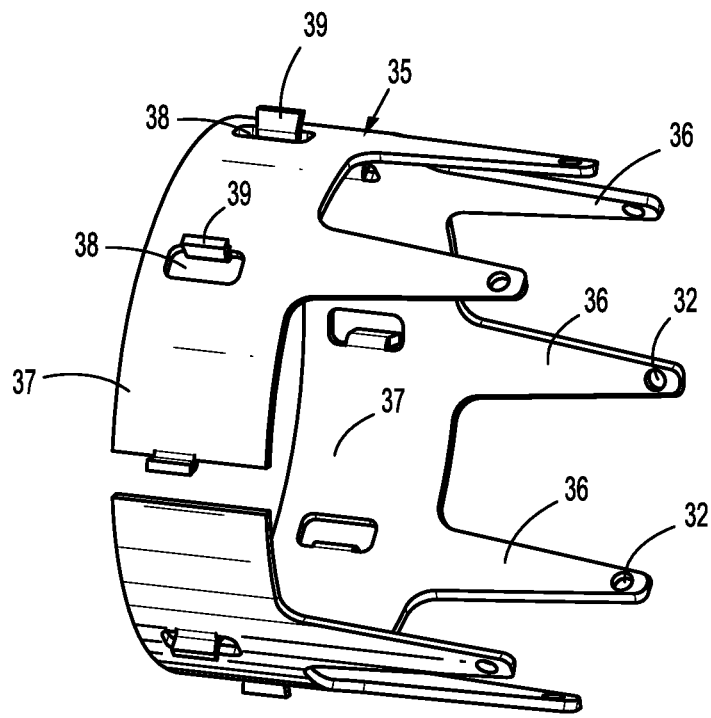
FIG. 10 is a perspective view of the release component of FIG. 4, illustrating a plurality of tabs used to retract the introducer sleeve, in accordance with an embodiment of the present disclosure.

Referring to FIG. 9, a cross-sectional view of the introducer sleeve 16 illustrating the plurality of tabs 45, 47 of the shell 31 extending from the plurality of openings 44, 46 of the introducer sleeve 16, in accordance with an embodiment of the present disclosure is presented. Referring to FIG. 10, a perspective view of the release component 35 of FIG. 4, illustrating a plurality of tabs 39 used to retract the introducer sleeve 16, in accordance with an embodiment of the present disclosure is presented.

As mentioned above, with reference to FIG. 4, there are three types of openings or slots defined across the surface of sleeve 16. The sleeve 16 includes a plurality of distal openings 44 and a plurality of proximal openings 46. The sleeve 16 also includes a plurality of slots 40 positioned between the plurality of distal openings 44 and a plurality of proximal openings 46. The plurality of slots 40 cooperate with a plurality of releaser tabs 39 of the releaser component 35, as shown in FIG. 10. The plurality of distal tabs 45 inhibit the sleeve 16 from sliding off the releaser component 35 and the shell 31 in a direction "A," as shown in FIG. 9. The plurality of proximal tabs 47 inhibit the sleeve 16 from sliding off the releaser component 35 and the shell 31 in a direction "B," as shown in FIG. 9. Thus, the releaser component 35 is configured to travel in a region "R," as illustrated in FIG. 9. In other words, the tabs 39 of the releaser component 35 move in slots 40 of sleeve 16 such that the plurality of distal tabs 44 limit movement of the releaser component 35 in direction "A," whereas the tabs 39 of the releaser component 35 move in slots 40 of sleeve 16 such that the plurality of proximal tabs 46 limit movement of the releaser component 35 in direction "B." As noted in FIG. 9, the distalmost end 41 of the slot 40 is aligned with the distal tab 45, whereas the proximalmost end 43 of the slot 40 is aligned with the proximal tab 47.

Figure 11:
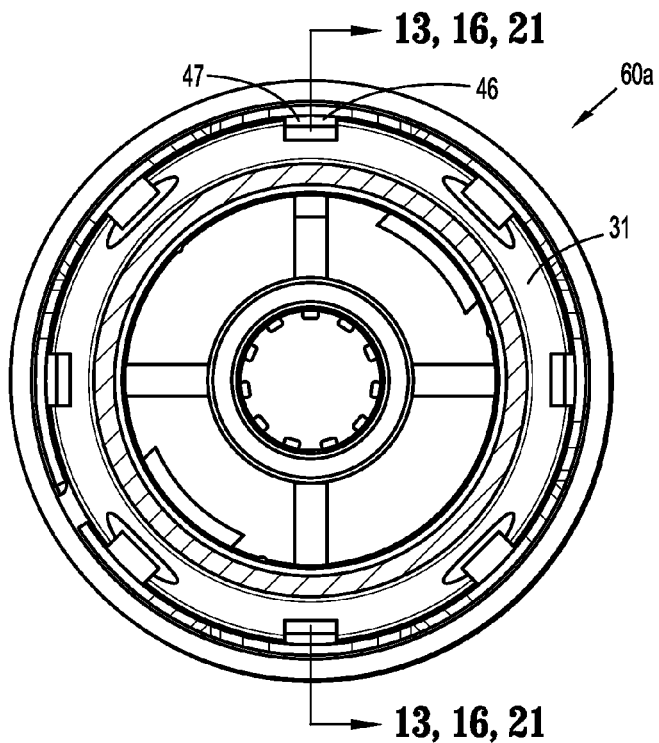
FIG. 11 is a front, cross-sectional view, along section line 11-11 of FIG. 2, in accordance with an embodiment of the present disclosure.
Figure 12:
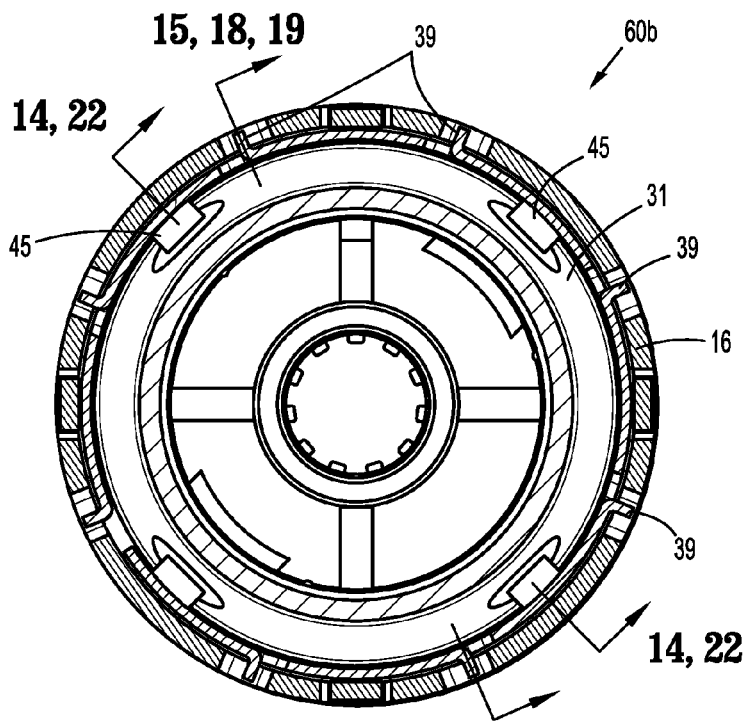
FIG. 12 is a front, cross-sectional view, along section line 12-12 of FIG. 4, in accordance with an embodiment of the present disclosure.

With reference to FIGS. 11 and 12, front, cross-sectional views 60a, 60b of the introducer sleeve 16 cooperating with the release component 35, in accordance with an embodiment of the present disclosure are presented.

FIG. 11 depicts the cross-sectional view 60a of the shell 31, where the tabs 47 protrude from the proximal openings 46, whereas FIG. 12 depicts the cross-sectional view 60b of the shell 31, where the sleeve 16 has been inserted over the shell 31. The tabs 39 of the releaser component 35 move within slots 40 of the sleeve 16 such that the plurality of proximal tabs 46 limit the movement of the releaser component 35. FIG. 12 clearly illustrates the interaction between the tabs 39 and the slots 40 of the sleeve 16.

Figure 13:
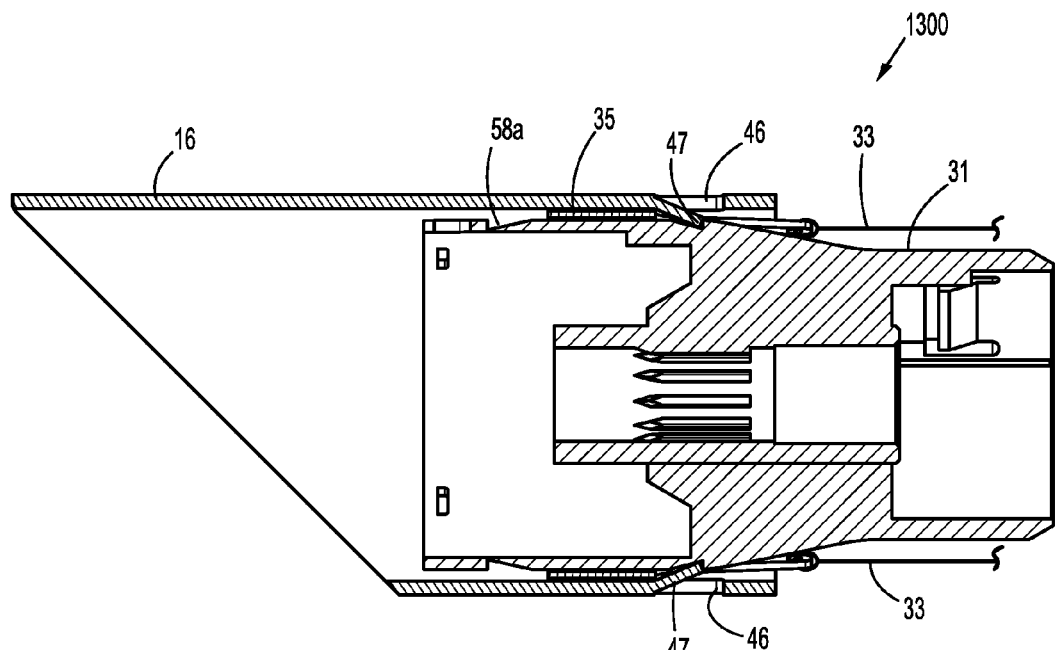
FIG. 13 is a cross-sectional view, along section line 13-13 of FIG. 11, of the introducer sleeve cooperating with the release component and the shell, such that either the proximal tabs or the distal tabs engage the plurality of grooves in the shell to inhibit the sleeve from sliding, in accordance with an embodiment of the present disclosure.
Figure 14:
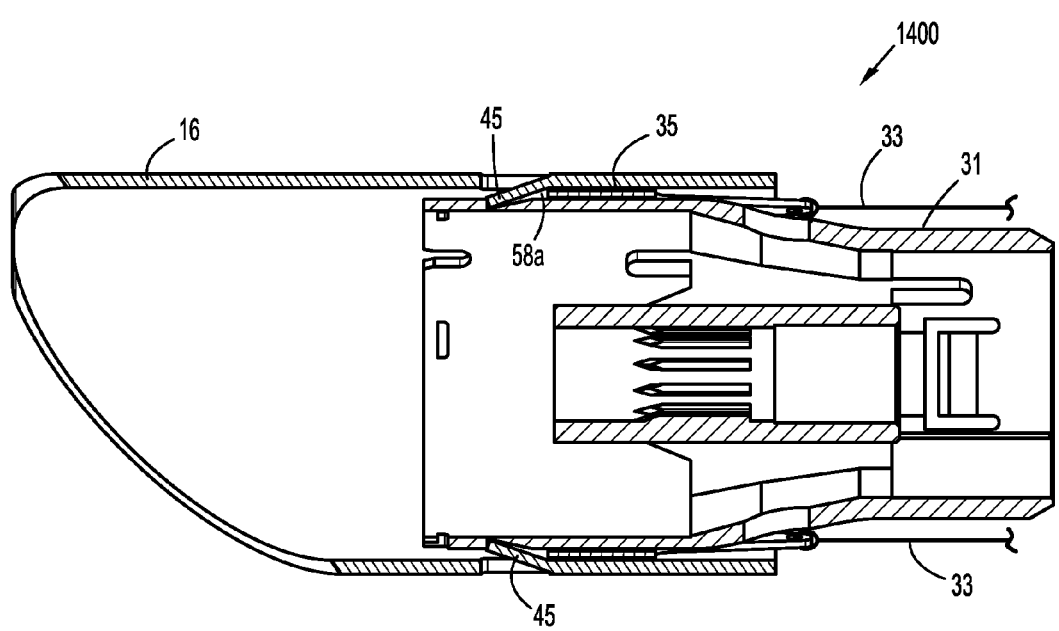
FIG. 14 is a cross-sectional view, along section line 14-14 of FIG. 12, of the introducer sleeve cooperating with the release component and the shell, such that either the proximal tabs or the distal tabs engage the plurality of grooves in the shell to inhibit the sleeve from sliding, in accordance with an embodiment of the present disclosure.

With reference to FIGS. 13-14, perspective views 1300, 1400 of the introducer sleeve 16 cooperating with the release component 35 and the shell 31, such that either the proximal tabs 46 or the distal tabs 45 engage the plurality of grooves 58a, b in the shell 31 to inhibit the sleeve 16 from sliding are presented.

In FIG. 13, the proximal tabs 47 engage individual grooves 58b in the shell 31 to inhibit the sleeve 16 from sliding back during insertion onto the shell 31. In FIG. 14, the distal tabs 45 engage the individual grooves 58a in the shell 31 to inhibit the sleeve from sliding forward. In other words, the proximal tabs 47 and the distal tabs 45 are adapted and dimensioned to maintain longitudinal movement of the shell 31 within a predetermined range, as defined in FIG. 9, by region "R." Thus, the movement of the shell 31 is confined within the slot 40 of the sleeve 16.

Figure 15:
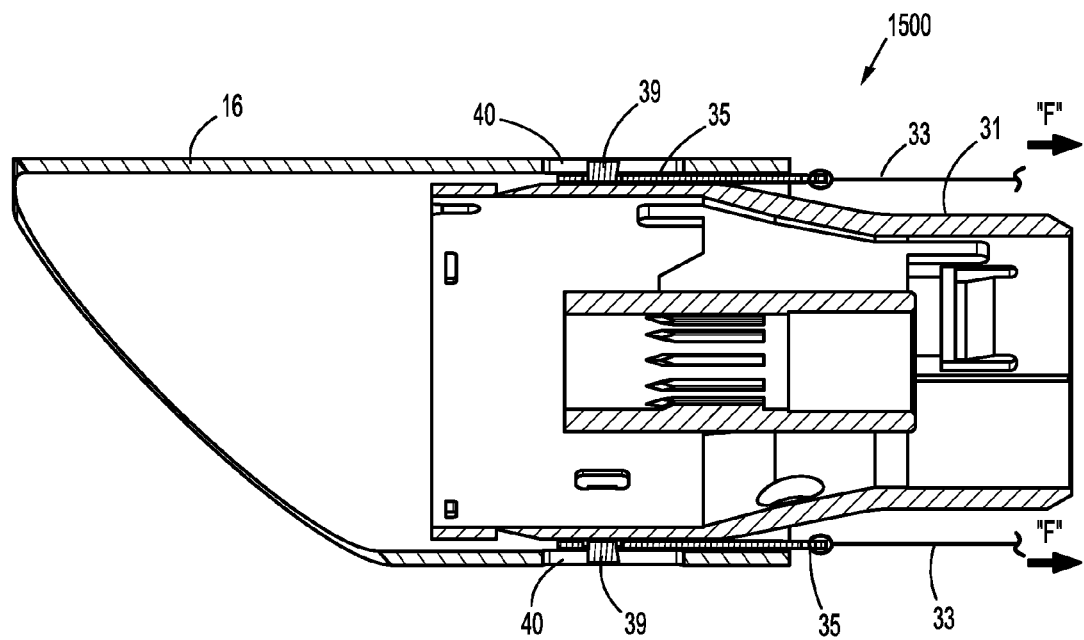
FIG. 15 is a cross-sectional view of the introducer sleeve locked in place to the shell, in accordance with an embodiment of the present disclosure.
Figure 16:
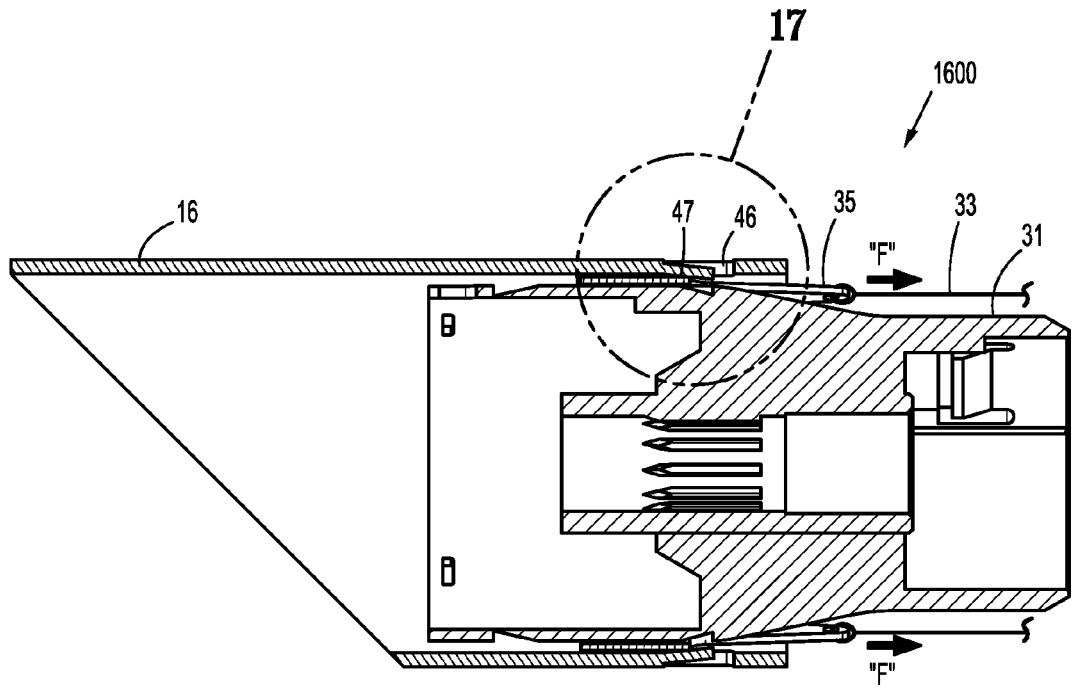
FIG. 16 is a cross-sectional view of the activation of the release component to enable the sleeve to be unlocked from the shell, in accordance with an embodiment of the present disclosure.

FIG. 15 is a perspective view 1500 of the introducer sleeve 16 locked in place to the shell 31, in accordance with an embodiment of the present disclosure, whereas FIG. 16 is a perspective view 1600 of the activation of the release component 35 to enable the sleeve 16 to be unlocked from the shell 31, in accordance with an embodiment of the present disclosure.

Figure 17:
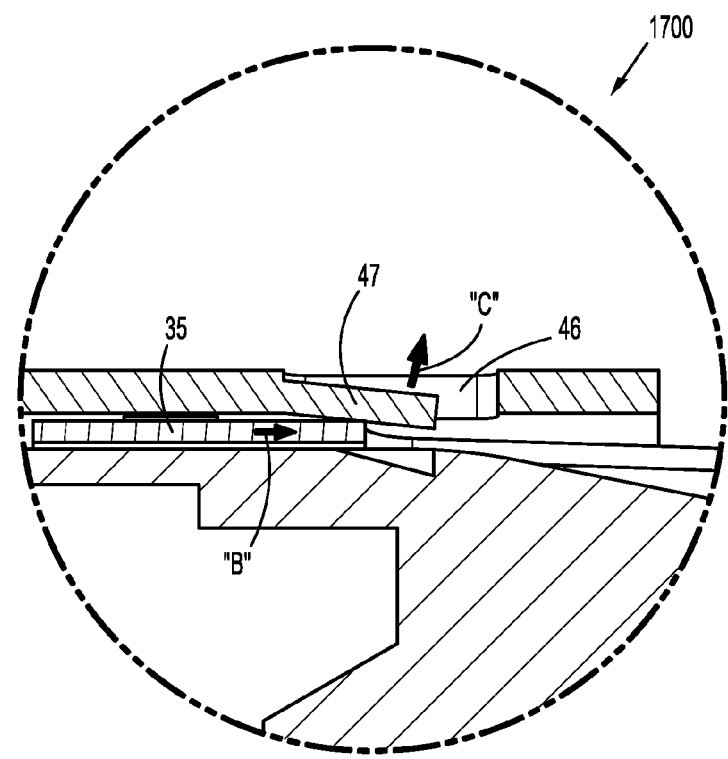
FIG. 17 is an area of detail of FIG. 16 depicting the release mechanism lifting the proximal tab of the sleeve, such that the sleeve disengages the shell, in accordance with an embodiment of the present disclosure.

In FIG. 15, the releaser tabs 39 contact or cooperate with the slot 40 of the sleeve 16. The releaser tab 39 slowly and steadily disengages from the slot 40 of the sleeve 16 by applying a force, "F," to releaser cables 33. The releaser cables 33 are connected to the body 37 of the releaser component 35, which in turn includes the releaser tabs 39. In FIG. 16, the force "F" is substantial enough to bias the releaser component 35 to the right, such that the releaser tab 39 also is forced to move to the right to disengage the slot 40 of the sleeve 16. At this point, in FIGS. 15 and 16, the disengagement has not yet occurred. FIG. 17 illustrates such point.

FIG. 17 is an enlarged view 1700 of the release mechanism lifting the proximal tab 47 of the sleeve 16, such that the sleeve 16 disengages the shell 31, in accordance with an embodiment of the present disclosure. In FIG. 17, the distal end of the releaser component 35 slides to the right, in a direction "B," such that the releaser component 35 pushes or biases the proximal tab 47 in an upward direction, indicated by arrow, "C." The proximal tab 47 extends upward past the opening 46 to allow the releaser component 35 to be removed from the shell 31 and the introducer sleeve 16. Thus, the releaser component 35 begins to move proximally such that the sleeve tabs 39 are finally disengaged from the grooves 58a, b of the shell 31.

Figure 18:
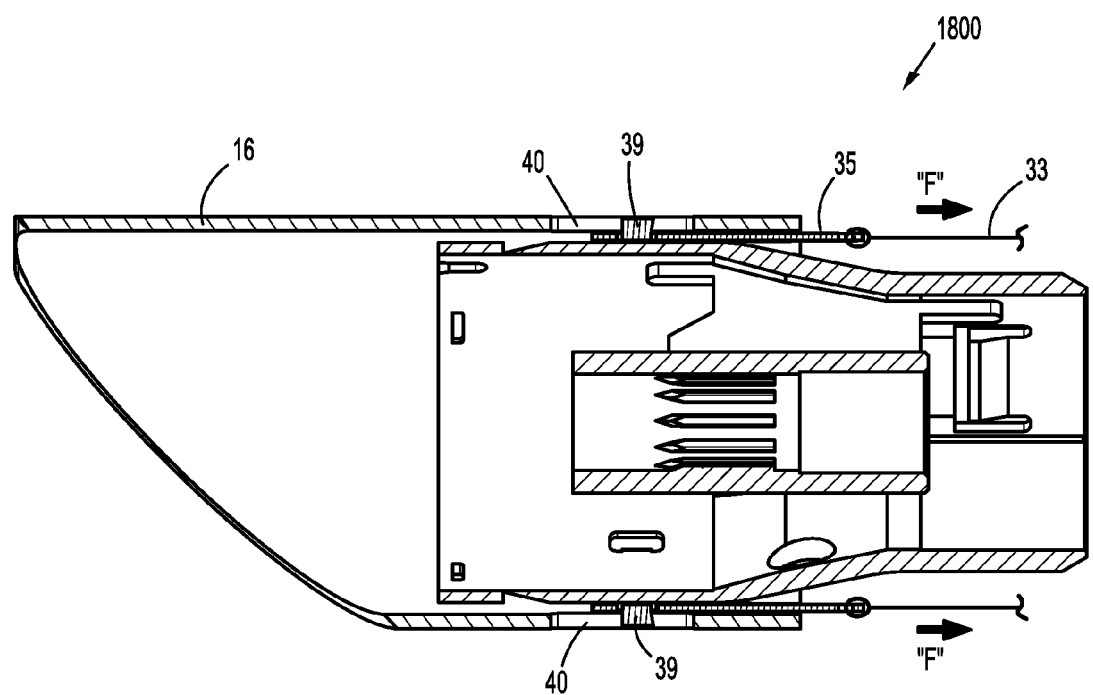
FIG. 18 illustrates the releaser tabs not yet reaching the end of the slots of the sleeve until after the sleeve tabs disengage from the plurality of grooves of the shell, in accordance with an embodiment of the present disclosure.
Figure 19:
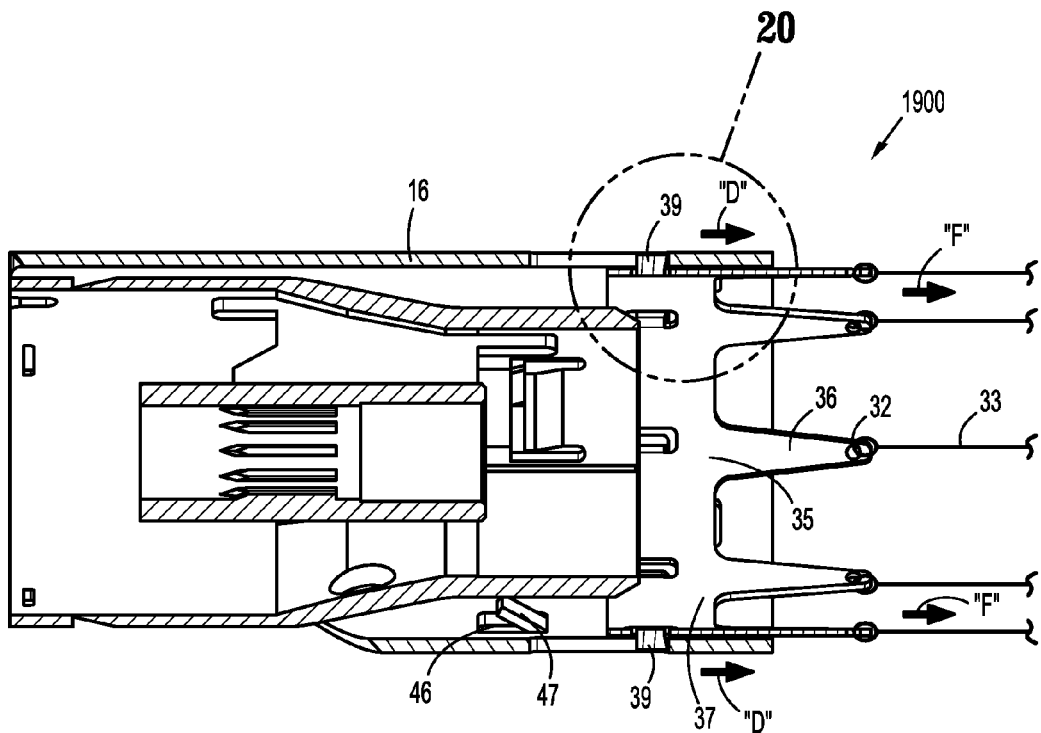
FIG. 19 illustrates, along section line 19-19 of FIG. 12, the releaser tabs reaching the end of the slots of the sleeve and pushing the sleeve off the shell, in accordance with an embodiment of the present disclosure.
Figure 20:
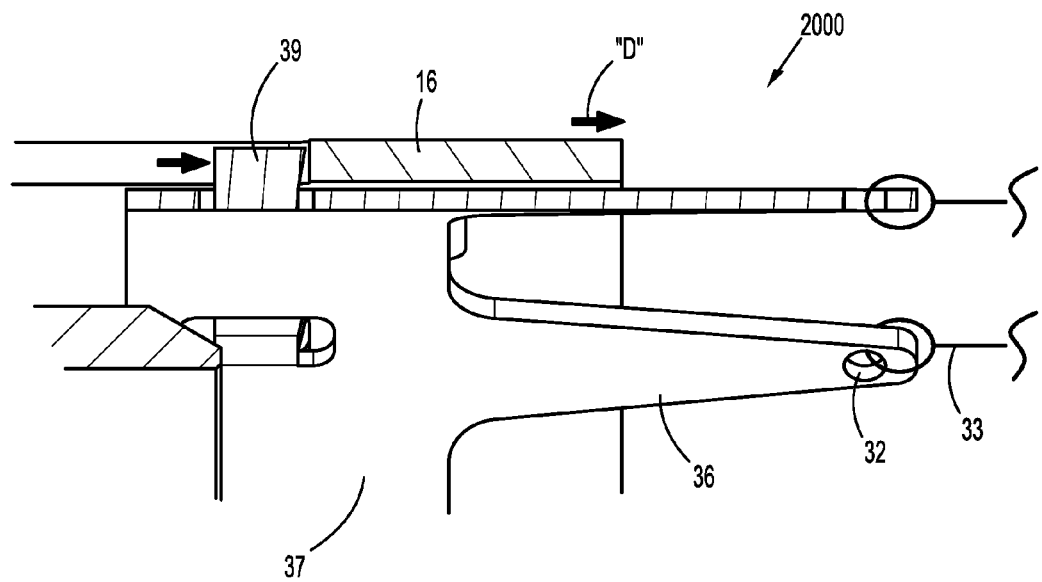
FIG. 20 is an area of detail of FIG. 19, in accordance with an embodiment of the present disclosure.

FIG. 18 illustrates a view 1800 where the releaser tabs 39 have not yet reached the end of the slots 40 of the sleeve 16 until after the releaser tabs 39 disengage from the plurality of grooves 58a, 58b of the shell 31. For example, at the bottom portion of FIG. 18, it is shown that the releaser tab 39 has moved more than halfway through the slots 40 toward the right, in direction "B." FIG. 19 illustrates a view 1900 where the releaser tabs 39 reach the end (proximalmost end) of the slots 40 of the sleeve 16 (direction "D") and push the sleeve 16 off the shell 31. FIG. 20 is an enlarged view 2000 of FIG. 19, in accordance with an embodiment of the present disclosure, clearly showing the releaser tab 39 moving in a direction "D" and contacting the proximalmost end of the slot 40 of the sleeve 16.

Figure 21:
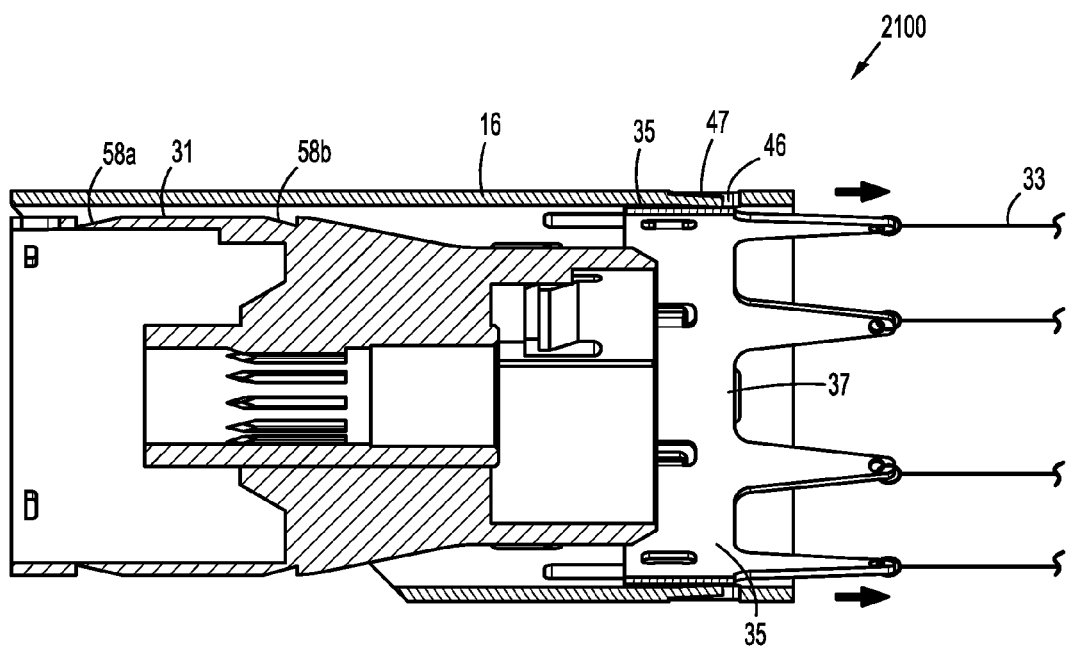
FIG. 21 illustrates, along section line 21-21 of FIG. 11, the sleeve in the retracted position being forced out by the releaser mechanism, in accordance with an embodiment of the present disclosure.
Figure 22:
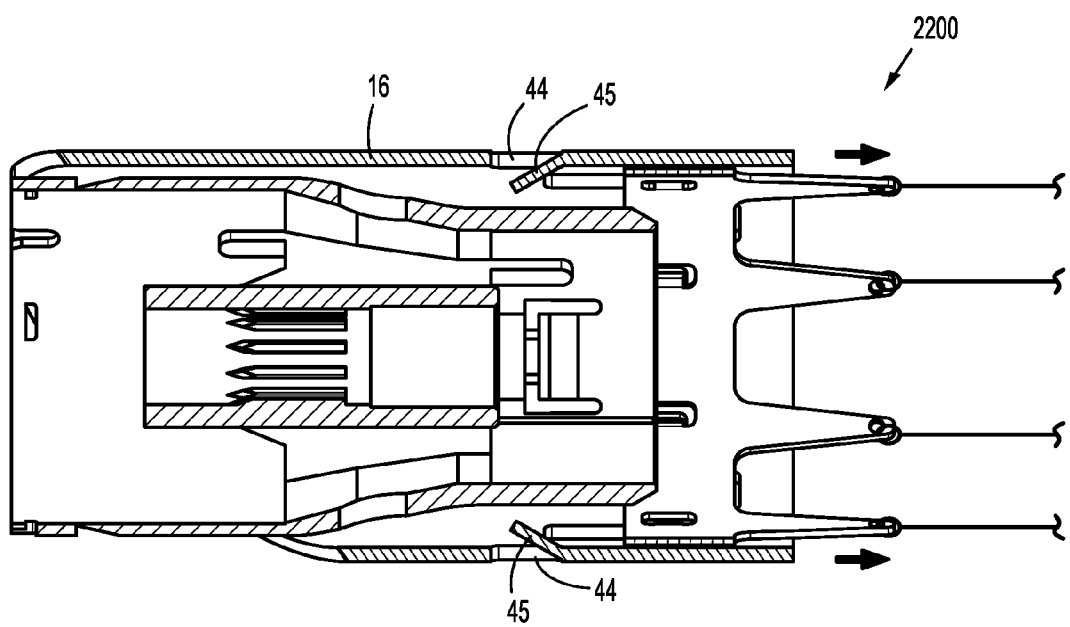
FIG. 22 illustrates, along section line 22-22 of FIG. 12, the sleeve in the retracted position being forced out by the releaser mechanism, in accordance with an embodiment of the present disclosure.

FIGS. 21-22 illustrate the sleeve 16 in the refracted position being forced out by the releaser mechanism 35, in accordance with an embodiment of the present disclosure. In FIG. 21, a view 2100 of the top portion of the releaser component 35 slidably engaging the proximal tab 47 is presented, which has been pushed outward by the release component 35. Additionally, the releaser component 35 has been disengaged from the plurality of grooves 58a, 58b of the shell 31. In FIG. 22, a view 2200 of the entire top portion of the releaser component 35 having slid past the proximal tab 47 is shown, such that the proximal tab 47 assumes its initial unbiased position. The releaser component 35 has now been completely removed from being lodged between the shell 31 and the introducer sleeve 16.

FIG. 23 illustrates an anvil assembly 2300 inserted through the introducer assembly 16, in accordance with an embodiment of the present disclosure. In FIG. 23, an anvil 2310 is inserted through the slit 19 of the membrane 17 of the sleeve 16. Additionally, as shown a portion of the shell 31 extends through the slit 19 of the membrane 17 of the sleeve 16. The anvil 2310 may mechanically cooperate with the shell 31 in order to advance through the slit 19 of the membrane 17 of the sleeve 16.

Therefore, in operation or use, in the exemplary embodiments of the present disclosure, a slanted introducer 16 is presented for aiding in the insertion of an EEA device. The exemplary embodiments of the present disclosure include a slanted sleeve 16 that has a slanted membrane 17 mounted thereto to keep the device clean and free of debris during, for example, a surgical procedure. The sleeve 16 includes at least two sets of tabs 45, 47. One set of tabs faces forward (distal end) 45 and another set of tabs faces backward (proximal end) 47. The tabs 45, 47 lock with the grooves 58a, b of the shell 31 in order to inhibit the sleeve 16 from traveling during insertion of the EEA device. Once the EEA device is inserted to the desired location, the sleeve 16 may be retracted back through the membrane 17 by pulling on the cables 33 attached to the releaser component 35. When the releaser component 35 is pulled back, it contacts or engages the tabs 45, 47 to lift the tabs 45, 47, thus releasing the sleeve 16 from the shell 31. The releaser component 35 may also include tabs that are accommodated within slots 40 on the sleeve 16, so that the tabs push against the sleeve 16 to retract the sleeve 16 when the sleeve 16 is pulled. As a result, the EEA device is inhibited from accumulating contaminants during its travel through a body cavity, thus keeping the staple line clean. Additionally, the slanted sleeve 16 provides a nice gradual ramp to aid navigation through the body cavity.

In certain embodiments, the sleeve has a cylindrical shape with a slanted end, and the membrane has a slanted surface. In any of the embodiments disclosed herein, the membrane and/or sleeve can have other shapes such as a bullet-shape or a curvilinear shape.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical stapling device, comprising:
   an elongated body portion having a proximal end and a distal end, and defining a longitudinal axis therethrough;
   a handle assembly positionable adjacent the elongated body portion at the proximal end thereof; and
   an introducer assembly positioned at the distal end of the elongated body portion, the introducer assembly including a sleeve positionable over at least a portion of a shell, the sleeve having a distal end defining a rim, the distal end being slanted relative to the longitudinal axis of the elongated body portion and receiving a slanted membrane over the rim.

2. The surgical stapling device according to claim 1, wherein a releaser component is positioned between the sleeve and the shell, the releaser component including a plurality of outwardly protruding tabs circumferentially disposed thereon and a plurality of cables circumferentially attached thereto.

3. The surgical stapling device according to claim 2, wherein a portion of the releaser component having the plurality of cables circumferentially attached thereto extends beyond a proximal end of the sleeve.

4. The surgical stapling device according to claim 2, wherein when a force is applied to the plurality of cables, the releaser component is slidingly displaced along the longitudinal axis of the elongated body portion to remove the sleeve from the shell.

5. The surgical stapling device according to claim 2, wherein the plurality of outwardly protruding tabs of the releaser component are lifted to disengage the sleeve from the shell during retraction of the sleeve.

6. The surgical stapling device according to claim 1, wherein the sleeve includes a plurality of first slots and a plurality of second slots circumferentially disposed at a proximal end thereof.

7. The surgical stapling device according to claim 6, wherein the plurality of second slots are configured to cooperate with a plurality of respective sleeve tabs extending therethrough, the plurality of sleeve tabs configured to secure the sleeve to the shell.

8. The surgical stapling device according to claim 7, wherein the plurality of sleeve tabs are forward facing tabs disposed at one end of the sleeve and rearward facing tabs disposed at the other end of the sleeve such that the sleeve moves longitudinally within a predetermined region defined by a distance between the forward facing and rearward facing tabs.

9. The surgical stapling device according to claim 6, wherein the plurality of first slots are configured to cooperate with a plurality of outwardly protruding tabs of a releaser component.

10. The surgical stapling device according to claim 1, wherein the shell includes at least one groove extending circumferentially therearound for allowing the shell to rotate.

11. The surgical stapling device according to claim 1, wherein the shell includes a plurality of grooves circumferentially disposed in equally spaced apart intervals thereon for inhibiting the shell from rotating.

12. The surgical stapling device according to claim 1, wherein the slanted membrane includes a slit extending a length of the slanted membrane.

13. An introducer assembly, comprising:
a shell;
a sleeve configured to be inserted over at least a portion of the shell, the sleeve having a distal end defining a rim, the distal end being slanted relative to the longitudinal axis of the elongated body portion and receiving a slanted membrane over the rim; and
a release mechanism located between the shell and the sleeve such that a portion of the release mechanism engages an inner surface of the sleeve to releasably couple the sleeve to the shell.

14. The introducer assembly according to claim 13, wherein the sleeve is a slanted sleeve configured to receive a slanted membrane having a slit thereon.

15. The introducer assembly according to claim 13, wherein the release mechanism includes a plurality of outwardly protruding tabs circumferentially disposed thereon and a plurality of cables circumferentially attached thereon.

16. The introducer assembly according to claim 15, wherein a portion of the release mechanism having the plurality of cables circumferentially attached thereto extends beyond a proximal end of the sleeve.

17. The introducer assembly according to claim 15, wherein when a force is applied to the plurality of cables, the release mechanism is slidingly displaced to remove the sleeve from the shell.

18. The introducer assembly according to claim 15, wherein the plurality of outwardly protruding tabs of the release mechanism are lifted to disengage the sleeve from the shell during retraction of the sleeve.

19. The introducer assembly according to claim 13, wherein the sleeve includes a plurality of first slots and a plurality of second slots circumferentially disposed at a proximal end thereof.

20. The introducer assembly according to claim 19, wherein the plurality of second slots are configured to cooperate with a plurality of respective sleeve tabs extending therethrough, the plurality of sleeve tabs configured to secure the sleeve to the shell.

21. The introducer assembly according to claim 20, wherein the plurality of sleeve tabs are forward facing tabs disposed at one end of the sleeve and rearward facing tabs disposed at the other end of the sleeve such that the sleeve moves longitudinally within a predetermined region defined by a distance between the forward facing and rearward facing tabs.

22. The introducer assembly according to claim 19, wherein the plurality of first slots are configured to cooperate with a plurality of outwardly protruding tabs of the release mechanism.

23. The introducer assembly according to claim 13, wherein the shell includes at least one groove extending circumferentially therearound for allowing the shell to rotate.

24. The introducer assembly according to claim 13, wherein the shell includes a plurality of grooves circumferentially disposed in equally spaced apart intervals thereon for inhibiting the shell from rotating.

* * * * *